US012685468B2

(12) United States Patent　　　(10) Patent No.:　US 12,685,468 B2
Aggarwal et al.　　　　　　　　　(45) Date of Patent:　　Jul. 21, 2026

(54) DEVICES, METHODS, AND SYSTEMS FOR IDENTIFYING A DRUNKEN DRIVER

(71) Applicant: Toyota Motor North America, Inc., Plano, TX (US)

(72) Inventors: Kush Aggarwal, McKinney, TX (US); Palak Bhargava, Irving, TX (US); Johns Roy, Frisco, TX (US); Darshan Vijaykumar, Modesto, CA (US); Angel Khushi Patel, Lewisville, TX (US); Kennedy Myles, Lancaster, TX (US); Vyshnavi Nalla, Irving, TX (US); Anna Shelukha, Salt Lake City, UT (US); Robert W. Douglas, II, Farmers Branch, TX (US); Nithila Shenoy, Leander, TX (US); Blake Garibaldi, McKinney, TX (US); Benjamin Jacob Thomas, Sunnyvale, TX (US); Nodoka Sasaki, Little Elm, TX (US); Sai Krishna Veeravelli, Plano, TX (US); Sumit Rashinkar, Oakdale (CA); Umer Rehman, Plano, TX (US); Vadim Vernydub, McKinney, TX (US); Yusei Harada, The Colony, TX (US); Andrew Gordon, Cedar Rapids, IA (US); Sangeeta Gupta, Frisco, TX (US); Joseph Cook, Frisco, TX (US); Chandan Mazumdar, McKinney, TX (US); Pankaj Devgun, Frisco, TX (US); Jaya Kumari, Plano, TX (US)

(73) Assignees: Toyota Motor North America, Inc., Plano, TX (US); Toyota Jidosha Kabushiki Kaisha, Toyota (JP)

( * ) Notice: Subject to any disclaimer, the term of this patent is extended or adjusted under 35 U.S.C. 154(b) by 378 days.

(21) Appl. No.: 18/198,627

(22) Filed: May 17, 2023

(65) Prior Publication Data
US 2024/0382123 A1　　Nov. 21, 2024

(51) Int. Cl.
　　*A61B 5/16*　　　(2006.01)
　　*A61B 5/00*　　　(2006.01)
　　*A61B 5/18*　　　(2006.01)

(52) U.S. Cl.
　　CPC ............... *A61B 5/162* (2013.01); *A61B 5/18* (2013.01); *A61B 5/4266* (2013.01);
　　　　　　　　　(Continued)

(58) Field of Classification Search
　　CPC ......... A61B 5/162; A61B 5/18; A61B 5/4266; A61B 5/4803; A61B 5/6893; A61B 2503/22
　　　　　　　　　(Continued)

(56) References Cited

U.S. PATENT DOCUMENTS 6,652,101 B1 * 11/2003 Glaser ................... A61B 3/032
　　　　　　　　　　　　　　351/239
9,775,565 B1 * 10/2017 Berg-Neuman ..... A61B 5/6893
　　　　　　　　　(Continued)

FOREIGN PATENT DOCUMENTS

CN　　203237052 U　10/2013

OTHER PUBLICATIONS westvirginiaduilawyers.com, The Wagner Law Firm, "3 Apps to Combat Drunk Driving", pp. 1-2, Dec. 2019, https://www.westvirginiaduilawyers.com/blog/2019/december/3-apps-to-combat-drunk-driving.

*Primary Examiner* — Naomi J Small
(74) *Attorney, Agent, or Firm* — Dinsmore & Shohl LLP

(57)　　　　　ABSTRACT
A device includes a controller configured to activate an application on the device, present a cognitive test through the application. The cognitive test includes a plurality of sub-tests including at least two of a typing accuracy and speed test, a speech slurring test, a reaction time test, a depth perception test, and a puzzle test. The controller is config-
(Continued)

ured to determine whether the driver passed each of the sub-tests based on inputs received from the driver, and determine whether the driver is drunken based on results of the sub-tests.

20 Claims, 9 Drawing Sheets

(52) U.S. Cl.
CPC .......... *A61B 5/4803* (2013.01); *A61B 5/6893* (2013.01); *A61B 2503/22* (2013.01)

(58) Field of Classification Search
USPC ........................................................ 340/576
See application file for complete search history.

(56) References Cited

U.S. PATENT DOCUMENTS

| | | | |
|---|---|---|---|
| 2007/0024454 A1 | 2/2007 | Singhal | |
| 2011/0304465 A1 | 12/2011 | Boult et al. | |
| 2012/0112879 A1 | 5/2012 | Ekchian et al. | |
| 2014/0062722 A1 | 3/2014 | Ofir et al. | |
| 2018/0121608 A1* | 5/2018 | Gross ..................... | G16H 20/30 |
| 2020/0156654 A1* | 5/2020 | Boss ........................ | A61B 5/12 |
| 2020/0372824 A1* | 11/2020 | Hanson .................. | G16H 10/60 |
| 2021/0291650 A1* | 9/2021 | Minjeur ................ | B60K 35/60 |
| 2021/0362750 A1* | 11/2021 | Yang ..................... | B60W 40/08 |
| 2022/0073079 A1* | 3/2022 | Nilsson ................ | G06V 10/764 |
| 2024/0326590 A1* | 10/2024 | Van Valer ............ | B60K 28/063 |

* cited by examiner

Click the Colored
Rectangles

I cant take this test

Repeat the Sentence

I don't know how
to play the
xylophone!

Next

I cant take this test

Welcome to SteerClear

We suspect you may be under
the influence in your vehicle.
Please continue to the test to
ensure your safety and get
access to your vehicle Start The Exam Click the Longer Line I can't take this test

*FIG. 2E*

Type these characters

SMEM

Type Here...

I can't take this test

*FIG. 2D*

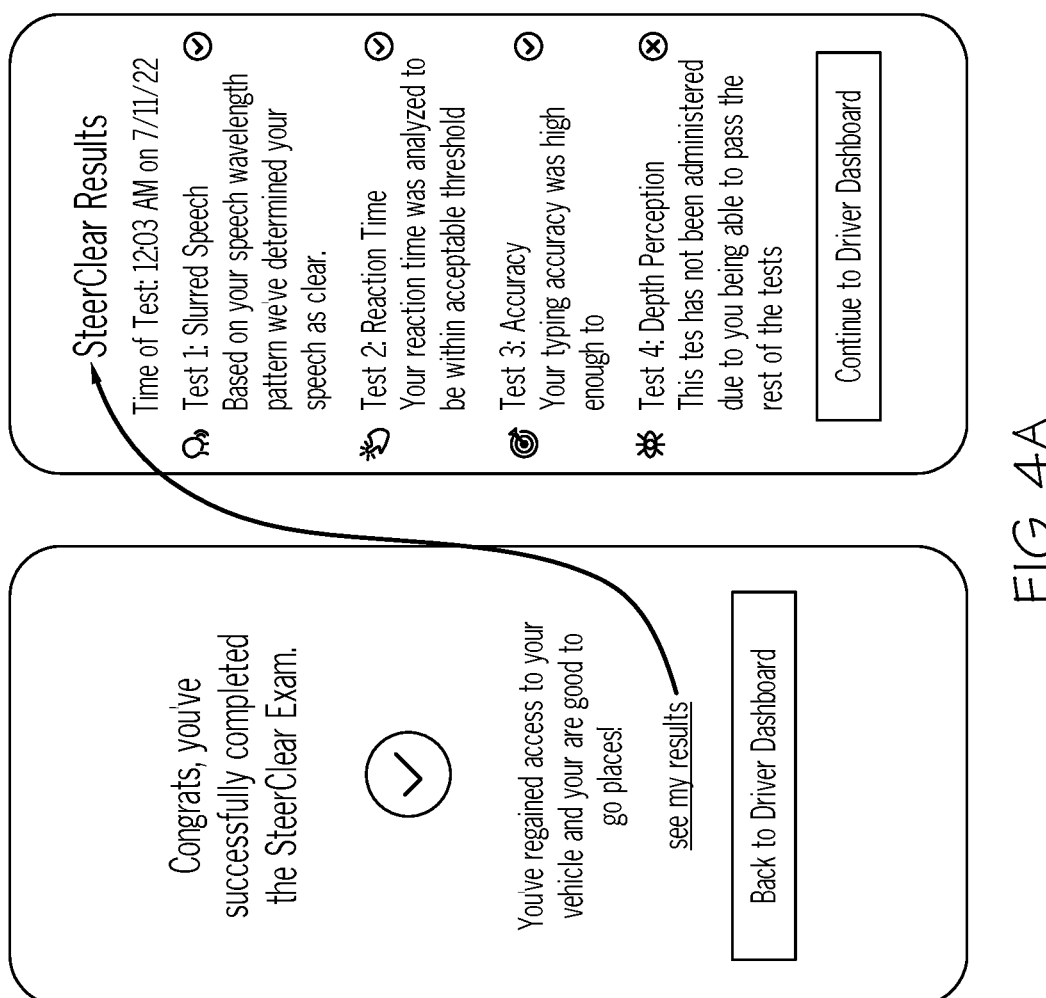

Congrats, you've successfully completed the SteerClear Exam.

You've regained access to your vehicle and your are good to go places!

see my results

Back to Driver Dashboard

SteerClear Results

Time of Test: 12:03 AM on 7/11/22

Test 1: Slurred Speech
Based on your speech wavelength pattern we've determined your speech as clear.

Test 2: Reaction Time
Your reaction time was analyzed to be within acceptable threshold Test 3: Accuracy
Your typing accuracy was high enough to Test 4: Depth Perception
This tes has not been administered due to you being able to pass the rest of the tests Continue to Driver Dashboard

FIG. 4A

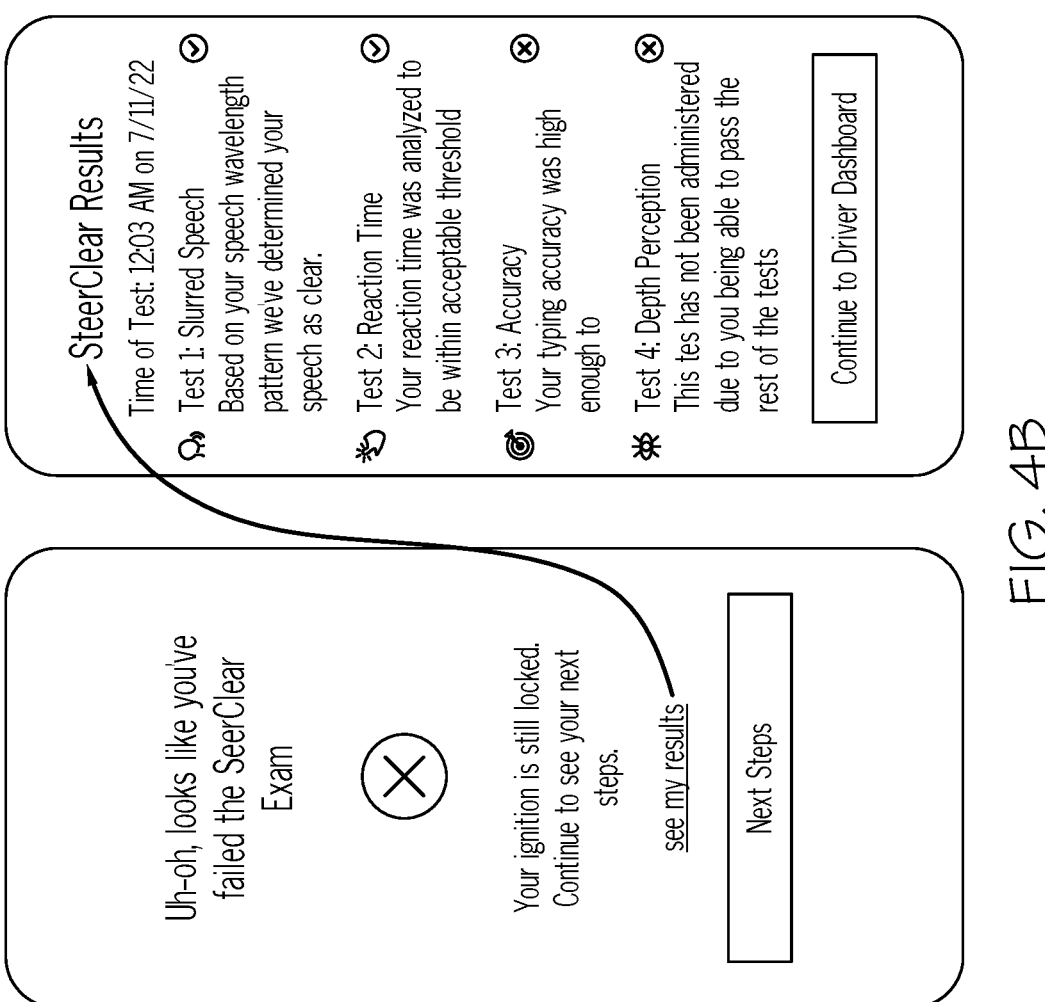

Uh-oh, looks like you've failed the SeerClear Exam

ⓧ

Your ignition is still locked. Continue to see your next steps.

see my results

Next Steps

SteerClear Results

Time of Test: 12:03 AM on 7/11/22

Test 1: Slurred Speech
Based on your speech wavelength pattern we've determined your speech as clear. ⊘

Test 2: Reaction Time
Your reaction time was analyzed to be within acceptable threshold ⊘

Test 3: Accuracy
Your typing accuracy was high enough to ⊗

Test 4: Depth Perception
This tes has not been administered due to you being able to pass the rest of the tests ⊗

Continue to Driver Dashboard

FIG. 4B

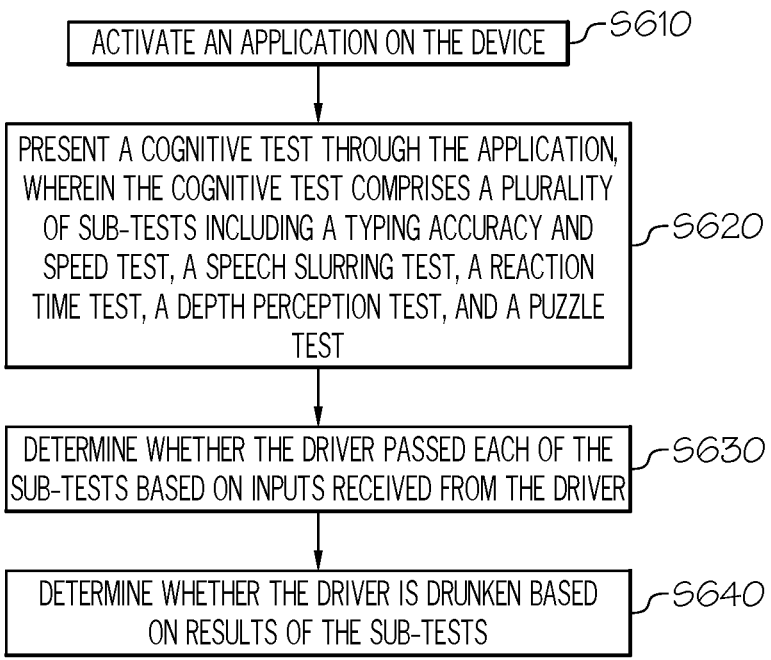

ACTIVATE AN APPLICATION ON THE DEVICE ⌐S610

PRESENT A COGNITIVE TEST THROUGH THE APPLICATION, WHEREIN THE COGNITIVE TEST COMPRISES A PLURALITY OF SUB-TESTS INCLUDING A TYPING ACCURACY AND SPEED TEST, A SPEECH SLURRING TEST, A REACTION TIME TEST, A DEPTH PERCEPTION TEST, AND A PUZZLE TEST ⌐S620

DETERMINE WHETHER THE DRIVER PASSED EACH OF THE SUB-TESTS BASED ON INPUTS RECEIVED FROM THE DRIVER ⌐S630

DETERMINE WHETHER THE DRIVER IS DRUNKEN BASED ON RESULTS OF THE SUB-TESTS ⌐S640

FIG. 6

DEVICES, METHODS, AND SYSTEMS FOR IDENTIFYING A DRUNKEN DRIVER

TECHNICAL FIELD

The present disclosure relates to devices, methods, and systems for identifying a drunken driver.

BACKGROUND

It may be desirable for a number of reasons to prevent drunken driving. Conventional systems may identify drunken drivers using sensors such as in-cabin image detectors, touch alcohol detectors, and breathe alcohol detectors. However, these conventional in-cabin detectors may not adequately identify drunken drivers. In addition, these conventional systems may require expensive hardware to be installed in the vehicle.

Accordingly, a need exists for devices, methods, and systems that accurately identify drunken drivers to mitigate situations caused by drunken driving.

SUMMARY

The present disclosure provides devices, methods, and systems for identifying a drunken driver by using a cognitive test comprising a plurality of sub-tests. With the cognitive test, the devices, methods, and systems accurately identify drunken drivers, thereby preventing drunken driving.

In one or more embodiments, a device includes a controller configured to activate an application on the device, present a cognitive test through the application, wherein the cognitive test comprises a plurality of sub-tests including at least two of a typing accuracy and speed test, a speech slurring test, a reaction time test, a depth perception test, and a puzzle test, determine whether a driver passed each of the sub-tests based on inputs received from the driver, and determine whether the driver is drunken based on results of the sub-tests.

In another embodiment, a method for identifying a drunken driver includes activating an application on a device, presenting a cognitive test through the application, wherein the cognitive test comprises a plurality of sub-tests including at least two of a typing accuracy and speed test, a speech slurring test, a reaction time test, a depth perception test, and a puzzle test, determining whether a driver passed each of the sub-tests based on inputs received from the driver, and determining whether the driver is drunken based on results of the sub-tests.

In yet another embodiment, a system of identifying a drunken driver includes a vehicle and a device. The vehicle includes a sensor. The device includes a controller configured to activate an application on the device, present a cognitive test through the application, wherein the cognitive test comprises a plurality of sub-tests including at least two of a typing accuracy and speed test, a speech slurring test, a reaction time test, a depth perception test, and a puzzle test, determine whether a driver passed each of the sub-tests based on inputs received from the driver, and determine whether the driver is drunken based on results of the sub-tests.

These and additional features provided by the embodiments of the present disclosure will be more fully understood in view of the following detailed description, in conjunction with the drawings.

BRIEF DESCRIPTION OF THE DRAWINGS

The following detailed description of specific embodiments of the present disclosure can be best understood when read in conjunction with the following drawings, where like structure is indicated with like reference numerals and in which:

FIGS. 2A-2F schematically depict an exemplary embodiment of cognitive test including a plurality of sub-tests, according to one or more embodiments shown and described herein;

FIGS. 4A-4B schematically depict an exemplary embodiment of the results of a cognitive test, according to one or more embodiments shown and described herein;

FIG. 6 depicts a flowchart for a method of identifying a drunken driver, according to one or more embodiments shown and described herein.

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

The embodiments disclosed herein include devices, methods, and systems for identifying a drunken driver by using a cognitive test. The cognitive test may be presented to a driver through an application on a device such as a smartphone. The cognitive test may include a plurality of sub-test including at least two of a typing accuracy and speed test, a speech slurring test, a reaction time test, a depth perception test, and a puzzle test. With the cognitive test, the devices, methods, and systems accurately identify drunken drivers, thereby preventing an undesirable situation, such as drunken driving.

Figure 1:
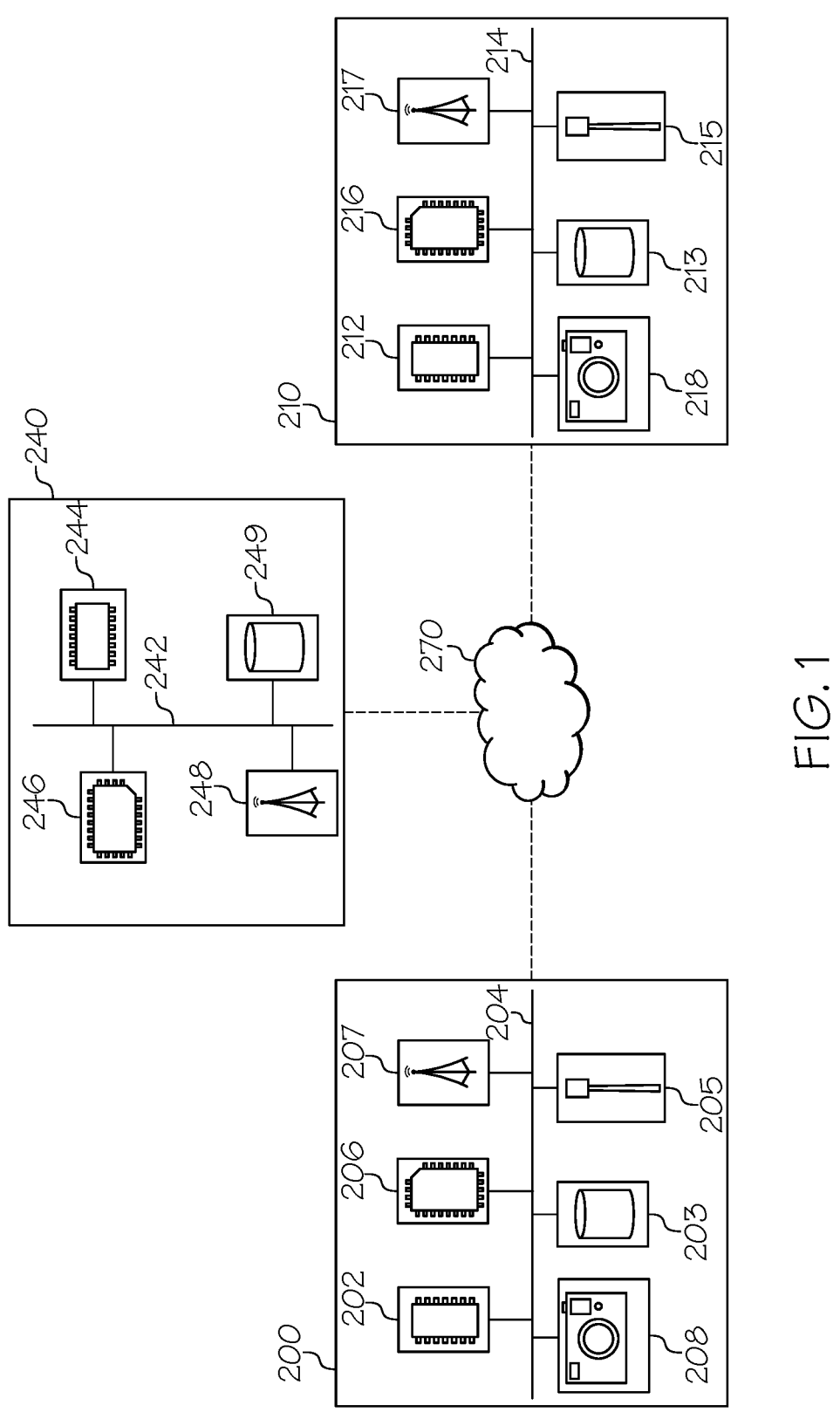
FIG. 1 depicts a schematic diagram of a system for identifying a drunken driver, according to one or more embodiments shown and described herein.

FIG. 1 depicts a schematic diagram of a system for identifying a drunken driver, according to one or more embodiments shown and described herein. The system includes a vehicle system 200, a device system 210, and a server 240.

It is noted that, while FIG. 1 depicts that the vehicle system 200 communicates with the device system 210. In embodiments, the vehicle system 200 may be included within a vehicle that may be an automobile or any other passenger or non-passenger vehicle such as, for example, a terrestrial, aquatic, and/or airborne vehicle. In some embodiments, the vehicle may be an autonomous vehicle that navigates its environment with limited human input or without human input.

The vehicle system 200 includes one or more processors 202. Each of the one or more processors 202 may be any device capable of executing machine-readable and executable instructions. Each of the one or more processors 202 may be a controller, an integrated circuit, a microchip, a computer, or any other computing device. One or more processors 202 are coupled to a communication path 204 that provides signal interconnectivity between various modules of the system. The communication path 204 may communicatively couple any number of processors 202 with one another, and allow the modules coupled to the communication path 204 to operate in a distributed computing environment. Each of the modules may operate as a node that may send and/or receive data. As used herein, the term "communicatively coupled" means that coupled components are capable of exchanging data signals with one another such as electrical signals via a conductive medium, electromagnetic signals via air, optical signals via optical waveguides, and the like.

The communication path 204 may be formed from any medium that is capable of transmitting a signal such as conductive wires, conductive traces, optical waveguides, or the like. In some embodiments, the communication path 204 may facilitate the transmission of wireless signals, such as WiFi, Bluetooth®, Near Field Communication (NFC), and the like. The communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors, memories, sensors, input devices, output devices, and communication devices. The communication path 204 may comprise a vehicle bus, such as a LIN bus, a CAN bus, a VAN bus, and the like. Additionally, it is noted that the term "signal" means a waveform (e.g., electrical, optical, magnetic, mechanical, or electromagnetic), such as DC, AC, sinusoidal-wave, triangular-wave, square-wave, vibration, and the like, capable of traveling through a medium.

The vehicle system 200 includes one or more memory modules 206 coupled to the communication path 204. One or more memory modules 206 may comprise RAM, ROM, flash memories, hard drives, or any device capable of storing machine-readable and executable instructions such that the machine-readable and executable instructions can be accessed by the one or more processors 202. The machine-readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine-readable and executable instructions and stored on the one or more memory modules 206. The machine-readable and executable instructions may be written in a hardware description language (HDL), such as logic implemented via either a field-programmable gate array (FPGA) configuration or an application-specific integrated circuit (ASIC), or their equivalents. The methods described herein may be implemented in any conventional computer programming language, as pre-programmed hardware elements, or as a combination of hardware and software components. The one or more processors 202 along with the one or more memory modules 206 may operate as a controller for the vehicle system 200.

Still referring to FIG. 1, the vehicle system 200 includes one or more sensors 208. One or more sensors 208 may be any device having an array of sensing devices capable of detecting radiation in an ultraviolet wavelength band, a visible light wavelength band, or an infrared wavelength band. One or more sensors 208 may detect the presence of the vehicle system 200, the distance between the vehicle system 200 and the device system 210, or both. One or more sensors 208 may have any resolution. In some embodiments, one or more optical components, such as a mirror, fish-eye lens, or any other type of lens may be optically coupled to one or more sensors 208. In some embodiments, one or more sensors 208 may provide image data to one or more processors 202 or another component communicatively coupled to the communication path 204. In some embodiments, one or more sensors 208 may provide navigation support. In embodiments, data captured by one or more sensors 208 may be used to autonomously or semi-autonomously navigate the vehicle system 200.

In some embodiments, one or more sensors 208 include one or more imaging sensors configured to operate in the visual and/or infrared spectrum to sense visual and/or infrared light. In some embodiments, one or more sensors 208 include one or more LIDAR sensors, radar sensors, sonar sensors, or other types of sensors for gathering data that could be integrated into or supplement the data collection. Ranging sensors like radar sensors may be used to obtain rough depth and speed information for the view of the vehicle system 200.

The vehicle system 200 includes a satellite antenna 205 coupled to the communication path 204 such that the communication path 204 communicatively couples the satellite antenna 205 to other modules of the vehicle system 200. The satellite antenna 205 is configured to receive signals from global positioning system satellites. In one embodiment, the satellite antenna 205 includes one or more conductive elements that interact with electromagnetic signals transmitted by global positioning system satellites. The received signal is transformed into a data signal indicative of the location (e.g., latitude and longitude) of the satellite antenna 205 or an object positioned near the satellite antenna 205, by one or more processors 202.

The vehicle system 200 includes one or more vehicle sensors 203. Each of one or more vehicle sensors 203 is coupled to the communication path 204 and communicatively coupled to one or more processors 202. One or more vehicle sensors 203 may include one or more motion sensors for detecting and measuring motion and changes in the motion of the vehicle system 200. The motion sensors may include inertial measurement units. Each of the one or more motion sensors may include one or more accelerometers and one or more gyroscopes. Each of one or more motion sensors transforms sensed physical movement of the vehicle into a signal indicative of an orientation, a rotation, a velocity, or an acceleration of the vehicle.

Still referring to FIG. 1, the vehicle system 200 includes a network interface hardware 207 for communicatively coupling the vehicle system 200 to the device system 210. The network interface hardware 207 may be communicatively coupled to the communication path 204 and may be any device capable of transmitting and/or receiving data via a network. The network interface hardware 207 may include a communication transceiver for sending and/or receiving any wired or wireless communication. For example, the network interface hardware 207 may include an antenna, a modem, LAN port, WiFi card, WiMAX card, mobile communications hardware, near-field communication hardware, satellite communication hardware and/or any wired or wireless hardware for communicating with other networks and/or devices. In one embodiment, the network interface hardware 207 includes hardware configured to operate in accordance with the Bluetooth® wireless communication protocol. The network interface hardware 207 of the vehicle system 200 may transmit its data to the device system 210. For example, the network interface hardware 207 of the vehicle system 200 may transmit vehicle data, location data, maneuver data, and the like to other objects, a cloud server, edge servers, and the like.

The vehicle system 200 may connect with one or more external vehicle systems and/or external processing devices (e.g., a cloud server, or an edge server) via a direct connection. The direct connection may be a vehicle-to-vehicle connection ("V2V connection"), a vehicle-to-everything connection ("V2X connection"), or a mmWave connection. The V2V or V2X connection or mm Wave connection may be established using any suitable wireless communication protocols discussed above. A connection between vehicles may utilize sessions that are time-based and/or location-based. In embodiments, a connection between vehicles or between a vehicle and an infrastructure element may utilize one or more networks to connect, which may be in lieu of, or in addition to, a direct connection (such as V2V, V2X, mmWave) between the vehicles or between a vehicle and an infrastructure. The vehicle system 200 may communicate with external communicate vehicle systems using wireless messages such as basic safety messages (BSMs), maneuver messages (MMs), and the like. BSM is a wireless message transmitted between vehicles where the transmitter sends its position, speed, and other static/dynamic information. MM is a general class of wireless messages exchanged between road users and infrastructure that contains the future trajectory (or possible future trajectories) of the transmitting road user. Specific examples of such messages could be the Maneuver Coordination Message (MCM) or the Maneuver Sharing Coordination Message (MSCM).

Vehicles may function as infrastructure nodes to form a mesh network and connect dynamically on an ad-hoc basis. In this way, vehicles may enter and/or leave the network at will, such that the mesh network may self-organize and self-modify over time. The network may include vehicles forming peer-to-peer networks with other vehicles or utilizing centralized networks that rely upon certain vehicles and/or infrastructure elements. The network may include networks using centralized servers and other central computing devices to store and/or relay information between vehicles.

Still referring to FIG. 1, the vehicle system 200 may be communicatively coupled to the device system 210, or the server 240 by the network 270. In one embodiment, the network 270 may include one or more computer networks (e.g., a personal area network, a local area network, or a wide area network), cellular networks, satellite networks and/or a global positioning system and combinations thereof. The vehicle system 200 may be communicatively coupled to the network 270 via a wide area network, a local area network, a personal area network, a cellular network, a satellite network, etc. Suitable local area networks may include wired Ethernet and/or wireless technologies such as Wi-Fi. Suitable personal area networks may include wireless technologies such as IrDA, Bluetooth®, Wireless USB, Z-Wave, ZigBee, and/or other near field communication protocols. Suitable cellular networks include, but are not limited to, technologies such as LTE, WiMAX, UMTS, CDMA, and GSM.

Still referring to FIG. 1, the device system 210 includes one or more processors 212, one or more memory modules 216, one or more sensors 218, one or more vehicle sensors 213, a satellite antenna 215, a network interface hardware 217, and a communication path 214 communicatively connected to the other components of device system 210. The components of the device system 210 may be structurally similar to and have similar functions as the corresponding components of the vehicle system 200 (e.g., the one or more processors 212 corresponds to the one or more processors 202, the one or more memory modules 216 corresponds to the one or more memory modules 206, the one or more sensors 218 corresponds to the one or more sensors 208, the satellite antenna 215 corresponds to the satellite antenna 205, the communication path 214 corresponds to the communication path 204, and the network interface hardware 217 corresponds to the network interface hardware 207).

Still referring to FIG. 1, the server 240 includes one or more processors 244, one or more memory modules 246, a network interface hardware 248, one or more vehicle sensors 249, and a communication path 242 communicatively connected to the other components of the vehicle system 200 and/or the other components of the device system 210. The components of the server 240 may be structurally similar to and have similar functions as the corresponding components of the vehicle system 200 (e.g., the one or more processors 244 corresponds to the one or more processors 202, the one or more memory modules 246 corresponds to the one or more memory modules 206, the one or more vehicle sensors 249 corresponds to the one or more vehicle sensors 203, the communication path 242 corresponds to the communication path 204, and the network interface hardware 248 corresponds to the network interface hardware 207).

It should be understood that the components illustrated in FIG. 1 are merely illustrative and are not intended to limit the scope of this disclosure. More specifically, while the components in FIG. 1 are illustrated as residing within the vehicle system 200, the device system 210, or both, this is a non-limiting example. In some embodiments, one or more of the components may reside external to the vehicle system 200, the device system 210, or both, such as with the server 240.

FIGS. 2A-2F schematically depict an exemplary embodiment of cognitive test including a plurality of sub-tests, according to one or more embodiments shown and described herein.

Referring to FIG. 2A-2F, the device may activate an application on the device. The device may include an output device of the vehicle, a display device of the driver, or both. The device may include a navigation device, a smartphone, a smartwatch, a laptop, a tablet computer, a personal computer, a wearable device, or combinations thereof.

In some embodiments, the application on the device may be activated in response to receiving instructions from the vehicle. For example, the vehicle may transmit the instructions to the device based on a result of comparing the current condition of the driver with a predetermined condition of the driver. The device may not activate the application when the current condition of the driver is similar or the same as the predetermined condition of the driver.

The sensor in the vehicle may detect a current condition of the driver. The current condition may comprise a current eye condition of the driver, a current body temperature of the driver, a current heart rate of the driver, or combinations thereof. The predetermined condition may be obtained from a database including data of the driver. The predetermined condition may be previously detected by the sensor in the vehicle when the driver was sober and passed a cognitive test. The predetermined condition may comprise a predetermined eye condition of the driver, a predetermined body temperature of the driver, a predetermined heart rate of the driver, or combinations thereof.

In some embodiments, the sensor may be disposed on a steering wheel and detect a current sweating condition of the driver. When a current sweating condition, such as a sweating value, of the driver is greater than a predetermined sweating condition of the driver, such as sweating condition of the driver when the driver is sober, the vehicle may transmit the instruction to the device and the device may activate the application on the device in response to receiving the instruction from the vehicle.

In some embodiments, the sensor may scan a current eye condition of the driver. When the current eye condition of the driver is different from a predetermined eye condition of the driver, such as an eye color of the driver when the driver is sober, the vehicle may transmit the instruction to the device and the device may activate the application on the device in response to receiving the instruction from the vehicle. For example, when the eye condition of the driver is redder than a predetermined eye condition of the driver, the vehicle may transmit the instruction to the device and the device may activate the application on the device in response to receiving the instruction from the vehicle.

In some embodiments, the sensor may detect a current body temperature of the driver. When the current body temperature of the driver is greater than a predetermined body temperature of the driver, such as a body temperature of the driver when the driver is sober, the vehicle may transmit the instruction to the device and the device may activate the application on the device in response to receiving the instruction from the vehicle.

In some embodiments, the sensor may detect a current heart rate of the driver. When the current heart rate of the driver is greater than a predetermined heart rate of the driver, such as a heart rate of the driver when the driver is sober, the vehicle may transmit the instruction to the device and the device may activate the application on the device in response to receiving the instruction from the vehicle.

In embodiments, the application may be activated by a user, time analysis, geolocation sensing, or combinations thereof. For example, the application may be activated by parents when the parents want to enforce the cognitive test for their child. In some embodiments, the application may be activated based on a range of intervals. For example, when the child is out past midnight and, in a location, where alcohols are easily accessible, then the application may be activated every time the child enters the vehicle. In some embodiments, when the child is out in the afternoon in a location where there may not provide alcohol, the application may be activated less frequently, such as once every 2 hours, when the child enters the vehicle. The frequency of activation may be determined by an algorithm that takes time and location via the device into consideration.

In response to activating the application, the device presents a cognitive test through the application. In some embodiments, in response to activating the application, the device notifies the driver about the cognitive test. For example, the device may provide an alarm, sounds, or both to the driver to notify the cognitive test.

The cognitive test may comprise a plurality of sub-tests. The plurality of sub-tests may include a typing accuracy and speed test, a speech slurring test, a reaction time test, a depth perception test, and a puzzle test.

Figures 2A, 2B, 2C:
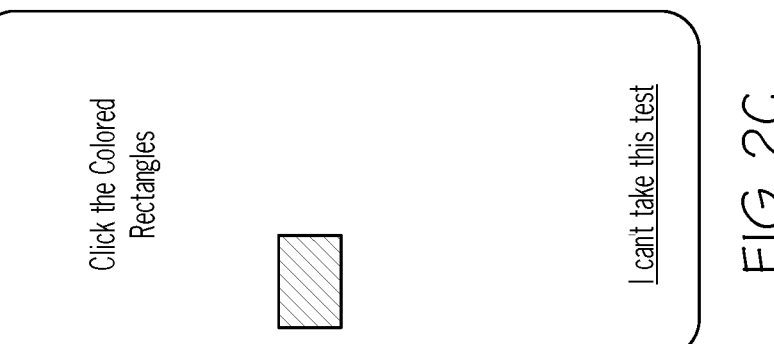

Referring to FIG. 2A, the cognitive test may be started with the instructions regarding the start of the cognitive test. For example, the cognitive test may start with the instruction "We suspect you may be under the influence in your vehicle. Please continue to the test to ensure your safety and get access to your vehicle." The driver may push the start button, such as "Start the exam."

Referring to FIG. 2B, the device may provide a speech slurring test. The speech slurring test may provide a sentence and ask the driver to repeat the sentence. For example, the speech slurring test may provide a sentence "I don't know how to play the xylophone." The device may record the sentence the driver said. The device may determine whether the driver passes the speech slurring test by analyzing a speech wavelength pattern of the input. For example, the device may compare a speech wavelength pattern of the input of the driver to a threshold speech wavelength pattern obtained from a database including speech wavelength patterns for sober drivers and speech wavelength patterns for drunken drivers. The speech wavelength patterns for sober drivers may show sharper and larger peaks and the speech wavelength patterns for drunken drivers may show smoother and smaller peaks. When the speech wavelength pattern of the input of the driver is similar or the same as a threshold speech wavelength pattern obtained from a database, the device may determine that the driver passes the speech slurring test. In some embodiments, the test may compare the length of the recorded speech with a predetermined length for the sentence to determine whether the driver passes the speech slurring test or not.

Referring to FIG. 2C, the device may provide a reaction time test. In one embodiment, the reaction time test may change a color of a screen of the application and ask the driver to push the screen when the color is changed. For example, the reaction time test may change the color of the screen from white to green and ask the driver to push the screen when the color is changed from white to color. In another embodiment, the reaction time test may provide an image and ask the driver to click the image. For example, the reaction time test may provide the colored rectangles and ask the driver to click the colored rectangles. The device may determine whether the driver passes the reaction time test by comparing a reaction time of the driver with a threshold time. For example, the device may compare a reaction time of the driver with a threshold time. The threshold time may be obtained from a database including reaction times for sober drivers and reaction times for drunken drivers. When the reaction time of the driver is similar or the same as the threshold time, the device may determine that the driver passes the reaction time test. When the reaction time of the driver deviates from the threshold time by a certain amount, the device may determine that the driver did not pass the reaction time test.

Figures 2D, 2E:
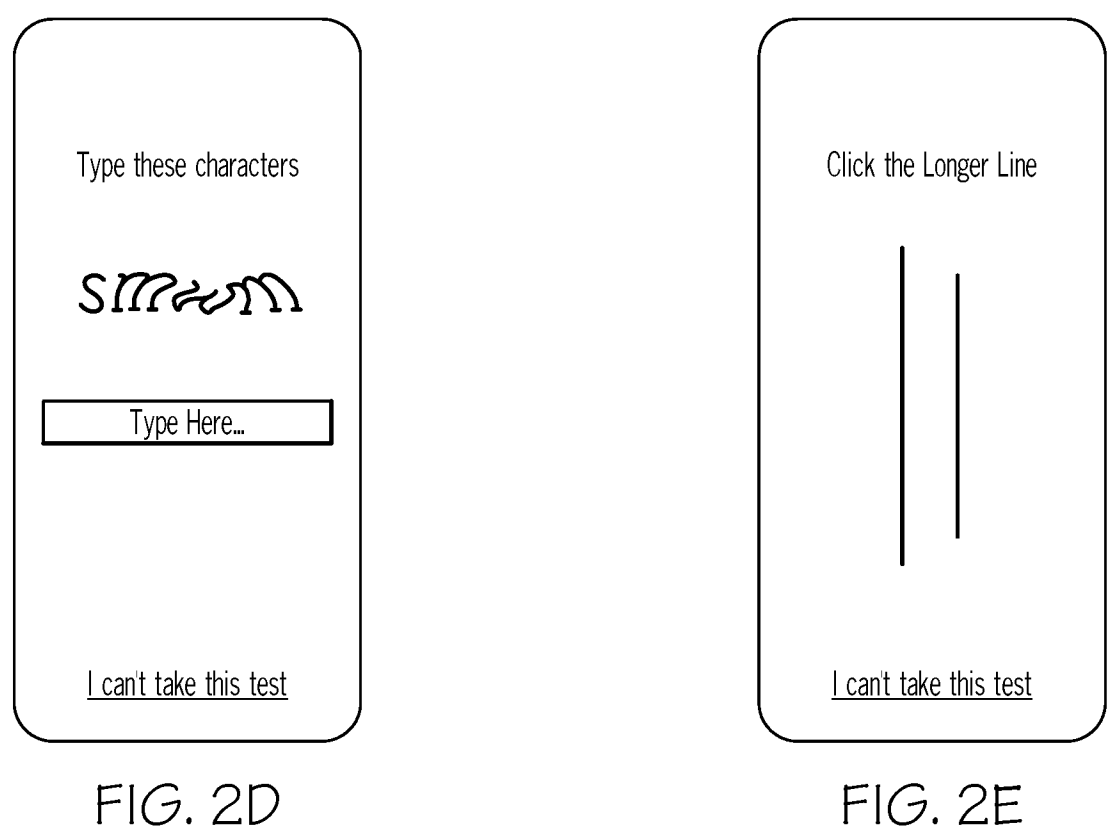

Referring to FIG. 2D, the device may provide a typing accuracy and speed test. In one embodiment, the typing accuracy and speed test may provide characters and ask the driver to type the characters. For example, the typing accuracy and speed test may provide the characters "SMWM" and ask the driver to type these characters. In another embodiment, the typing accuracy and speed test provides letters from an audio clip and ask the driver to type the letters. The device may determine whether the driver passes the typing accuracy and speed test by comparing a typing accuracy and speed of the driver with a threshold typing accuracy and speed. For example, the device may compare a typing accuracy and speed of the driver with a threshold typing accuracy and speed. The threshold typing accuracy and speed may be obtained from a database including typing accuracy and speed for sober drivers and typing accuracy and speed for drunken drivers. When the typing accuracy and speed of the driver are similar or the same as a threshold typing accuracy and speed, the device may determine that the driver passes the typing accuracy and speed test.

Referring to FIG. 2E, the device may provide a depth perception test. In one embodiment, the depth perception test may provide images and ask the driver to click a specific image. For example, the depth perception test may provide two lines and ask the driver to click the longer line. In another embodiment, the depth perception test may provide two lines and ask the driver to click if the two lines are parallel. The device may determine whether the driver passes the depth perception test by a correct input of the driver. For example, when the driver clicks the longer line or when two lines are parallel, the device may determine that the driver passes the depth perception test. When the driver clicks the shorter line or when two lines are not parallel, the device may determine that the driver does not pass the depth perception test. In some embodiments, the depth perception test may ask a second attempt.

Figure 2F:
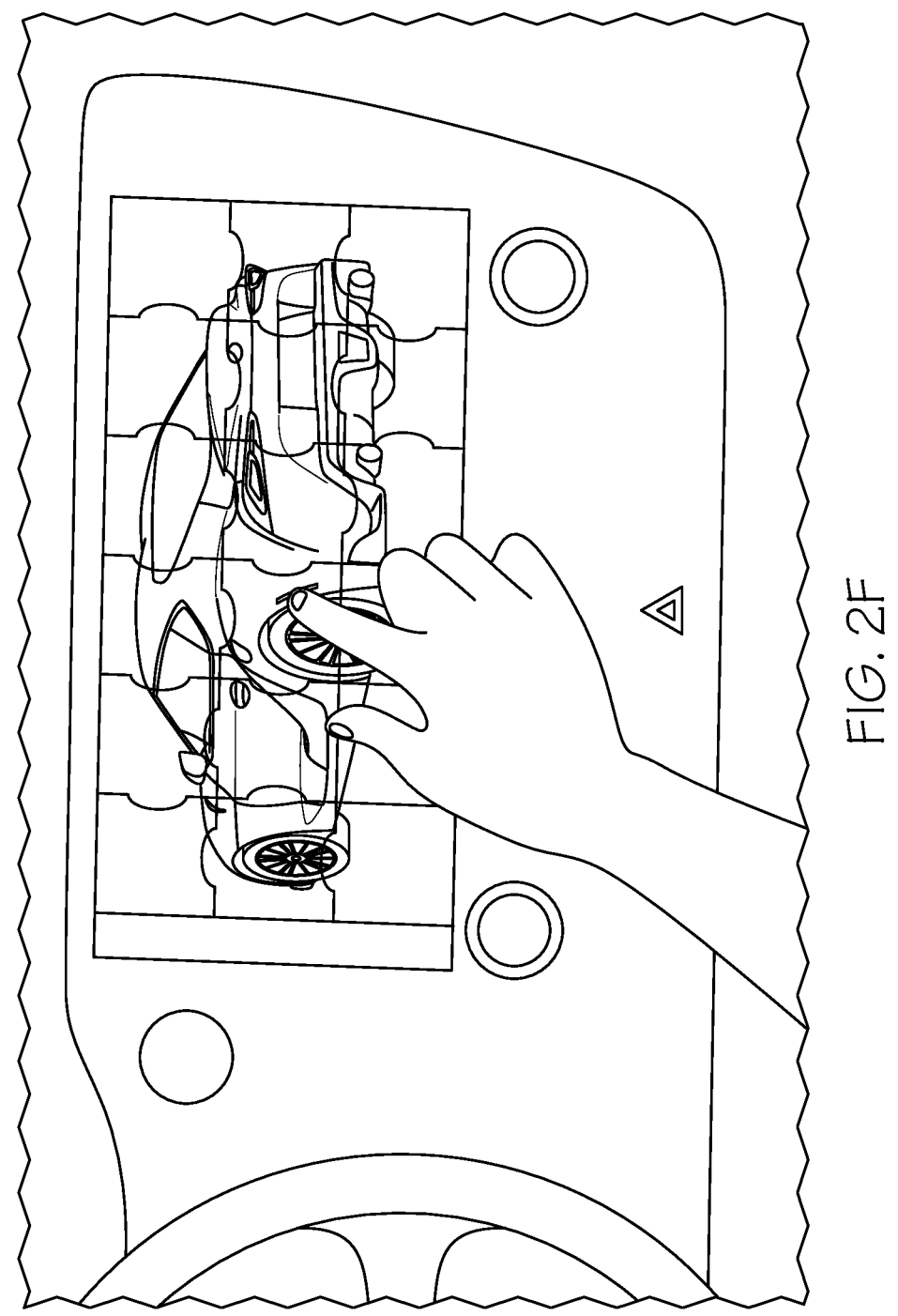

Referring to FIG. 2F, the device may provide a puzzle test. The puzzle test may provide puzzles and ask the driver to complete the puzzles by dragging at least one of the puzzles. The device may determine whether the driver passes the puzzle test by comparing a speed of dragging puzzles and the precision of the driver with a threshold speed of dragging puzzles and precision. For example, the device may compare a speed of dragging puzzles and the precision of the driver with a threshold speed of dragging puzzles and precision. The threshold speed of dragging puzzles and precision may be obtained from a database including the speed of dragging puzzles and the precision for sober drivers and the speed of dragging puzzles and the precision for drunken drivers. When the speed of dragging puzzles and the precision of the driver are similar or the same as the threshold speed of dragging puzzles and precision, the device may determine that the driver passes the puzzle test. In some embodiments, the puzzle test may ask a second attempt.

Figure 3:
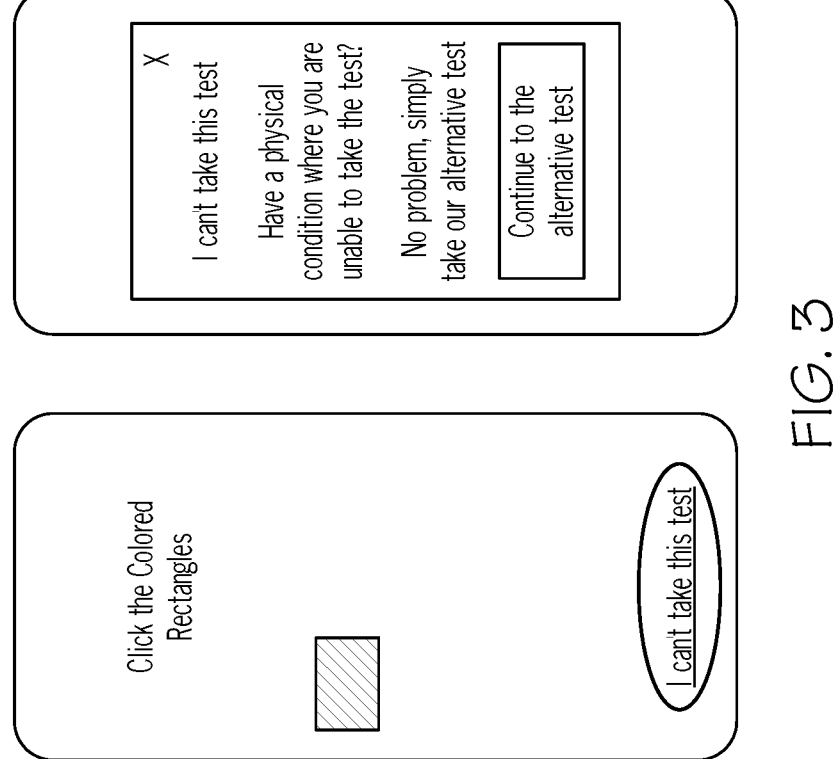
FIG. 3 schematically depicts an exemplary embodiment of indicating unavailability of taking a cognitive test, according to one or more embodiments shown and described herein.

Referring to FIG. 3, in some embodiments, the device may receive an input from the driver indicating that the driver is not able to take one of the sub-tests. When the device provides the sub-tests, the device provides an option to receive an input from the driver. For example, the device provides an option indicating "I can't take this test." When the driver clicks the option indicating "I can't take this test," the device may present an alternative sub-test. For example, when the driver has a speech impediment and the driver clicks the option indicating "I can't take this test" for a speech slurring test, the device may provide an alternative sub-test, such as a typing accuracy and speed test, a reaction time test, a depth perception test, and a puzzle test. For example, when the driver has a hand tremor and the driver clicks the option indicating "I can't take this test" for at least one of a typing accuracy and speed test, a reaction time test, a depth perception test, and a puzzle test, the device may provide an alternative sub-test, such as a speech slurring test. For example, when the driver has color blindness and the driver clicks the option indicating "I can't take this test" for a reaction time test, the device may provide an alternative sub-test, such as a typing accuracy and speed test, a speech slurring test, a depth perception test, and a puzzle test. When the driver clicks the option indicating "I can't take this test" for at least one of a typing accuracy and speed test, a speech slurring test, a reaction time test, a depth perception test, and a puzzle test and the driver cannot take these tests for any reasons, the device may connect the driver to an emergency call or a service representative of the vehicle to determine whether the driver is drunken.

In some embodiments, a profile for the driving is stored in the device. The profile may include information about tests that the driver is not able to test. For example, the profile for a driver A may store information that the driver A is color-blind. When the device identified the driver A, e.g., based on log-in information or recognition of the face of the driver A, the device may present tests excluding a test requires color recognition.

Referring to FIGS. 4A and 4B, the device may determine whether the driver passed each of the sub-tests based on inputs received from the driver. The device may notify a result of the cognitive test to the driver. For example, the device may display all results of sub-tests on the application.

The device determines whether the driver is drunken based on the results of the sub-tests. In some embodiments, when the driver passes at least three among five sub-tests, the device may determine that the driver is not drunken. In some embodiments, when the driver passes less than three among five sub-tests, the device may determine that the driver is drunken.

Figure 5:
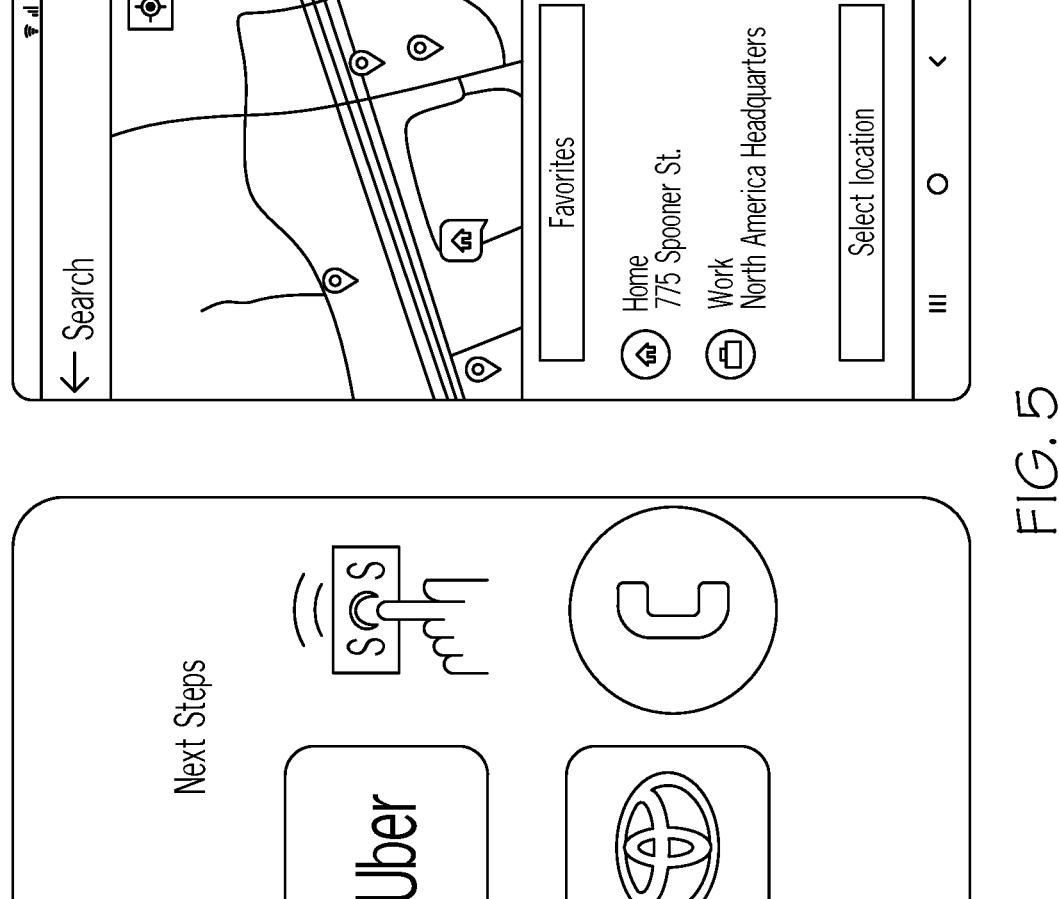
FIG. 5 schematically depicts an exemplary embodiment of providing an alternative of driving a vehicle to the driver, according to one or more embodiments shown and described herein.

Referring to FIG. 5, in response to determining that the driver is drunken, the device may lock a vehicle. The device may provide a ride-share request, an emergency call, or both. The device may share a digital key of the vehicle and give an access to a new designated driver.

In response to determining that the driver is sober, the device may notify the driver that the driver is able to start the vehicle. The device may allow the driver to start the ignition and drive the vehicle.

FIG. 6 depicts a flowchart for a method of identifying a drunken driver, according to one or more embodiments shown and described herein.

Referring to FIG. 6, in step S610, the controller may activate an application on the device. The controller may be included in the device, the vehicle, the server, road-side units, cameras, or combinations thereof. In some embodiments, the application may be activated in response to receiving an instruction from the vehicle. In another embodiment, the application may be activated by a user, time analysis, geolocation sensing, or combinations thereof.

The vehicle may transmit instructions for activating the application to the device based on a result of comparing a current condition of the driver with a predetermined condition of the driver. For example, a sensor in the vehicle may detect the current condition of the driver. The current condition may comprise a current eye condition of the driver, a current body temperature of the driver, a current heart rate of the driver, or combinations thereof. The predetermined condition may be obtained from a database including data of the driver. The predetermined condition may be previously detected by the sensor in the vehicle when the driver was sober and passed a cognitive test and stored in the device, the vehicle, or a server. The predetermined condition may comprise a predetermined eye condition of the driver, a predetermined body temperature of the driver, a predetermined heart rate of the driver, or combinations thereof.

In some embodiments, the sensor may be disposed on a steering wheel and detect a current sweating condition of the driver. When a current sweating condition, such as a sweating value, of the driver is greater than a predetermined sweating condition of the driver, such as the sweating condition of the driver when the driver is sober, the vehicle may transmit the instruction to the device and the device may activate the application on the device in response to receiving the instruction from the vehicle.

In some embodiments, the sensor may scan a current eye condition of the driver. When the current eye condition of the driver is different from a predetermined eye condition of the driver, such as an eye color of the driver when the driver is sober, the vehicle may transmit the instruction to the device and the device may activate the application on the device in response to receiving the instruction from the vehicle. For example, the eye condition of the driver is redder than a predetermined eye condition of the driver, the vehicle may transmit the instruction to the device and the device may activate the application on the device in response to receiving the instruction from the vehicle.

In some embodiments, the sensor may detect a current body temperature of the driver. When the current body temperature of the driver is greater than a predetermined body temperature of the driver, such as a body temperature of the driver when the driver is sober, the vehicle may transmit the instruction to the device and the device may activate the application on the device in response to receiving the instruction from the vehicle.

In some embodiments, the sensor may detect a current heart rate of the driver. When the current heart rate of the driver is greater than a predetermined heart rate of the driver, such as a heart rate of the driver when the driver is sober, the vehicle may transmit the instruction to the device and the device may activate the application on the device in response to receiving the instruction from the vehicle.

Referring back to FIG. 6, in step S620, the controller may present a cognitive test through the application. In some embodiments, in response to activating the application, the controller notifies the driver about the cognitive test. The cognitive test may comprise a plurality of sub-tests. Referring to FIGS. 2A-2F, the plurality of sub-tests may include a typing accuracy and speed test, a speech slurring test, a reaction time test, a depth perception test, and a puzzle test. Referring to FIG. 2A, the controller may provide the instructions regarding the start of the cognitive test. For example, the cognitive test may start with the instruction "We suspect you may be under the influence in your vehicle. Please continue to the test to ensure your safety and get access to your vehicle." The driver may push the start button, such as "Start the exam." The controller may receive the input from the driver. Referring to FIG. 2B, the controller may provide a speech slurring test. The speech slurring test may provide a sentence and ask the driver to repeat the sentence. For example, the speech slurring test may provide a sentence "I don't know how to play the xylophone." The controller may record the sentence the driver said. Referring to FIG. 2C, the controller may provide a reaction time test. In one embodiment, the reaction time test may change a color of a screen of the application and ask the driver to push the screen when the color is changed. For example, the reaction time test may change the color of the screen from white to green and ask the driver to push the screen when the color is changed from white to color. In another embodiment, the reaction time test may provide an image and ask the driver to click the image. For example, the reaction time test may provide the colored rectangles and ask the driver to click the colored rectangles. Referring to FIG. 2D, the controller may provide a typing accuracy and speed test. In one embodiment, the typing accuracy and speed test may provide characters and ask the driver to type the characters. For example, the typing accuracy and speed test may provide the characters "SMWM" and ask the driver to type these characters. In another embodiment, the typing accuracy and speed test provides letters from an audio clip and ask the driver to type the letters. Referring to FIG. 2E, the controller may provide a depth perception test. In one embodiment, the depth perception test may provide images and ask the driver to click the specific image. For example, the depth perception test may provide two lines and ask the driver to click the longer line. In another embodiment, the depth perception test may provide two lines and ask the driver to click if the two lines are parallel. Referring to FIG. 2F, the controller may provide a puzzle test. The puzzle test may provide puzzles and ask the driver to complete the puzzles by dragging at least one of the puzzles.

Referring back to FIG. 6, in step S630, the controller may determine whether the driver passed each of the sub-tests based on inputs received from the driver. The controller may compare an input of the driver in the cognitive test to a threshold value obtained from a database including data for sober drivers and data for drunken drivers. In some embodiments, the database including data for sober drivers and data for drunken drivers may be built by machine learning.

For example, referring to FIG. 2B, the controller may determine whether the driver passes the speech slurring test by analyzing a speech wavelength pattern of the input. For example, the controller may compare a speech wavelength pattern of the input of the driver to a threshold speech wavelength pattern obtained from a database including speech wavelength patterns for sober drivers and speech wavelength patterns for drunken drivers. When the speech wavelength pattern of the input of the driver is similar or the same as a threshold speech wavelength pattern obtained from a database, the controller may determine that the driver passes the speech slurring test.

Referring to FIG. 2C, the controller may determine whether the driver passes the reaction time test by comparing a reaction time of the driver with a threshold time. For example, the controller may compare a reaction time of the driver with a threshold time. The threshold time may be obtained from a database including reaction times for sober drivers and reaction times for drunken drivers. When the reaction time of the driver is similar or the same as a threshold reaction time, the controller may determine that the driver passes the reaction time test.

Referring to FIG. 2D, the controller may determine whether the driver passes the typing accuracy and speed test by comparing a typing accuracy and speed of the driver with a threshold typing accuracy and speed. For example, the controller may compare a typing accuracy and speed of the driver with a threshold typing accuracy and speed. The threshold typing accuracy and speed may be obtained from a database including typing accuracy and speed for sober drivers and typing accuracy and speed for drunken drivers. When the typing accuracy and speed of the driver are similar or the same as a threshold typing accuracy and speed, the controller may determine that the driver passes the typing accuracy and speed test.

Referring to FIG. 2E, the controller may determine whether the driver passes the depth perception test by a correct input of the driver. For example, when the driver clicks the longer line or when two lines are parallel, the device may determine that the driver passes the depth perception test. When the driver clicks the shorter line or when two lines are not parallel, the device may determine that the driver does not pass the depth perception test.

Referring to FIG. 2F, the controller may determine whether the driver passes the puzzle test by comparing a speed of dragging puzzles and the precision of the driver with a threshold speed of dragging puzzles and precision. For example, the controller may compare a speed of dragging puzzles and the precision of the driver with a threshold speed of dragging puzzles and precision. The threshold speed of dragging puzzles and precision may be obtained from a database including the speed of dragging puzzles and the precision for sober drivers and the speed of dragging puzzles and the precision for drunken drivers. When the speed of dragging puzzles and the precision of the driver are similar or the same as a threshold speed of dragging puzzles and precision, the controller may determine that the driver passes the puzzle test.

Referring back to FIG. 6, the controller may further receive an input from the driver indicating that the driver is not able to take one of the sub-tests. When the controller provides the sub-tests, the controller provides an option to receive an input from the driver. For example, by referring to FIG. 3, the controller provides an option indicating "I can't take this test." When the driver clicks the option indicating "I can't take this test," the controller may present an alternative sub-test. For example, when the driver has a speech impediment and the driver clicks the option indicating "I can't take this test" for a speech slurring test, the device may provide an alternative sub-test, such as a typing accuracy and speed test, a reaction time test, a depth perception test, and a puzzle test. For example, when the driver has a hand tremor and the driver clicks the option indicating "I can't take this test" for at least one of a typing accuracy and speed test, a reaction time test, a depth perception test, and a puzzle test, the device may provide an alternative sub-test, such as a speech slurring test. For example, when the driver has a color blindness and the driver clicks the option indicating "I can't take this test" for a reaction time test, the device may provide an alternative sub-test, such as a typing accuracy and speed test, a speech slurring test, a depth perception test, and a puzzle test. When the driver clicks the option indicating "I can't take this test" for at least one of a typing accuracy and speed test, a speech slurring test, a reaction time test, a depth perception test, and a puzzle test and the driver cannot take these tests for any reasons, the device may connect the driver to an emergency call or a service representative of the vehicle to determine whether the driver is drunken.

Referring back to FIG. 6, in step S640, the controller may determine whether the driver passed each of the sub-tests based on inputs received from the driver. The controller may notify a result of the cognitive test to the driver. For example, the controller may display all results of sub-tests on the application. By referring to FIGS. 4A and 4B, the controller may determine whether the driver passed each of the sub-tests based on inputs received from the driver. In some embodiments, when the driver passes at least three among five sub-tests, the controller may determine that the driver is not drunken. In some embodiments, when the driver passes less than three among five sub-tests, the controller may determine that the driver is drunken.

In some embodiments, in response to determining that the driver is drunken, the controller may lock a vehicle. For example, by referring to FIG. 5, the controller may provide a ride-share request, an emergency call, or both. The controller may share a digital key of the vehicle and give an access to a new designated driver.

In response to determining that the driver is sober, the controller may notify the driver that the driver is able to start the vehicle. The controller may allow the driver to start the ignition and drive the vehicle.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

The order of execution or performance of the operations in examples of the disclosure illustrated and described herein is not essential unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

What is claimed is:

1. A device comprising:
a controller configured to:
activate an application on the device;
present a cognitive test through the application, wherein the cognitive test comprises a plurality of sub-tests including at least two of a typing accuracy and speed test, a speech slurring test, a reaction time test, a depth perception test, and a puzzle test, wherein the plurality of sub-tests included in the cognitive test are based on a driver profile associated with a driver, and wherein the driver profile comprises information about one or more sub-tests that are unsuitable for the driver based on attributes of the driver;
determine whether the driver passed each of the sub-tests based on inputs received from the driver; and
determine whether the driver is drunken based on results of the sub-tests.

2. The device according to claim 1, wherein the plurality of sub-tests includes the speech slurring test, and the controller determines whether the driver passes the speech slurring test by analyzing a speech wavelength pattern of at least one input of the inputs.

3. The device according to claim 1, wherein the plurality of sub-tests includes the reaction time test, and the controller determines whether the driver passes the reaction time test by comparing a reaction time of the driver with a threshold time.

4. The device according to claim 1, wherein to activate the application is based on one or more of activation by a user, time analysis, geolocation sensing, or a current condition of the driver.

5. The device according to claim 1, wherein in response to activating the application, the controller is further configured to notify the driver about the cognitive test.

6. The device according to claim 1, wherein the controller is further configured to receive an input from the driver indicating that the driver is not able to take one of the sub-tests.

7. The device according to claim 6, wherein in response to receiving the input indicating that the driver is not able to take one of the sub-tests, the controller is configured to present an alternative sub-test.

8. The device according to claim 1, wherein in response to determining that the driver is drunken, the controller is configured to lock a vehicle and provide a ride share request, an emergency call, or both.

9. The device according to claim 1, wherein the controller is further configured to compare an input of the driver in the cognitive test to a threshold value obtained from a database including data for sober drivers and data for drunken drivers.

10. A method for identifying a drunken driver comprising:
activating an application on a device;
presenting a cognitive test through the application, wherein the cognitive test comprises a plurality of sub-tests including at least two of a typing accuracy and speed test, a speech slurring test, a reaction time test, a depth perception test, and a puzzle test, wherein the plurality of sub-tests included in the cognitive test are based on a driver profile associated with a driver, and wherein the driver profile comprises information about one or more sub-tests that are unsuitable for the driver based on attributes of the driver;
determining whether the driver passed each of the sub-tests based on inputs received from the driver; and
determining whether the driver is drunken based on results of the sub-tests.

11. The method according to claim 10, wherein the plurality of sub-tests includes the speech slurring test, and the method further comprises determining whether the driver passes the speech slurring test by analyzing a speech wavelength pattern of at least one input of the inputs.

12. The method according to claim 10, wherein the plurality of sub-tests includes the reaction time test, and the method further comprises determining whether the driver passes the reaction time test by comparing a reaction time of the driver with a threshold time.

13. The method according to claim 10, wherein to activate the application is based on one or more of activation by a user, time analysis, geolocation sensing, or a current condition of the driver.

14. The method according to claim 10, further comprising:
receiving an input from the driver indicating that the driver is not able to take one of the sub-tests; and
presenting an alternative sub-test.

15. The method according to claim 10, wherein in response to determining that the driver is drunken, and the method further comprises locking a vehicle and providing a ride share request, an emergency call, or both.

16. The method according to claim 10, further comprising comparing an input of the driver in the cognitive test to a threshold value obtained from a database including data for sober drivers and data for drunken drivers.

17. A system of identifying a drunken driver, the system comprising
a vehicle including a sensor; and
a device comprising:
a controller configured to:
activate an application on the device;
present a cognitive test through the application, wherein the cognitive test comprises a plurality of sub-tests including at least two of a typing accuracy and speed test, a speech slurring test, a reaction time test, a depth perception test, and a puzzle test, wherein the plurality of sub-tests included in the cognitive test are based on a driver profile associated with a driver, and wherein the driver profile comprises information about one or more sub-tests that are unsuitable for the driver based on attributes of the driver;
determine whether the driver passed each of the sub-tests based on inputs received from the driver; and
determine whether the driver is drunken based on results of the sub-tests.

18. The system according to claim 17, wherein:
the vehicle transmits an instruction to the device in response to the sensor detecting a predetermined condition of the driver; and
the controller activates the application on the device in response to receiving the instruction from the vehicle.

19. The system according to claim 18, wherein the sensor is disposed on a steering wheel, and the predetermined condition is a sweating condition of the driver.

20. The system according to claim 18, wherein the predetermined condition comprises a predetermined eye condition of the driver, a predetermined body temperature of the driver, a predetermined heart rate of the driver, or combinations thereof.

* * * * *